United States Patent [19]

Wang

[11] Patent Number: 5,502,055

[45] Date of Patent: Mar. 26, 1996

[54] TREATMENT OF ENDOTOXIC SHOCK WITH PUTRESCINE

[75] Inventor: Soo-Ray Wang, Taipei, Taiwan

[73] Assignee: National Science Council, Taipei, Taiwan

[21] Appl. No.: 510,582

[22] Filed: Aug. 2, 1995

[51] Int. Cl.⁶ .................................................. A61K 31/495
[52] U.S. Cl. ....................................................... 514/250
[58] Field of Search ............................................ 514/250

[56] References Cited

U.S. PATENT DOCUMENTS

| | | | |
|---|---|---|---|
| 4,761,417 | 8/1988 | Maroko | 514/284 |
| 5,153,178 | 10/1992 | Maroko | 514/26 |
| 5,436,270 | 7/1995 | Wang | 514/565 |

*Primary Examiner*—Raymond Henley, III
*Attorney, Agent, or Firm*—W. Wayne Liauh

[57] ABSTRACT

The present invention provides a method for protecting a living subject from endotoxic shock. The method involves administering to the subject a pharmaceutical composition including an effective amount of putrescine and a pharmaceutically acceptable carrier.

6 Claims, No Drawings

TREATMENT OF ENDOTOXIC SHOCK WITH PUTRESCINE

BACKGROUND OF THE INVENTION

1. Field of the Invention

The present invention relates to a method for treating endotoxic shock by administering to a living subject an effective amount of putrescine and a pharmaceutically acceptable carrier.

2. Description of the Prior Art

Endotoxin is a lipopolysaccharide molecule which is contained in the cell wall of all gram-negative bacteria. When a patient is infected with the bacteria, which is accompanied by hypotension and signs of poor tissue perfusion, it is called endotoxic shock. Many severely-ill patients die of endotoxic shock.

One of the most difficult problems in treating endotoxic shock lies in the fact that the mechanism causing endotoxic shock has not been fully understood, or may have been incorrectly stated.

The inventor of the present invention has found that arginase and L-arginine have a protective effect against lipopolysaccharide (LPS)-induced endotoxic shock in mice, which is disclosed in Taiwanese Patent Application No. 81110533 (now pending), U.S. patent application Ser. No. 08/044,233 (now allowed), and U.S. patent application Ser. No. 08/443,538 (now pending).

Since arginase can degrade L-arginine to L-ornithine and urea, L-ornithine can be converted to putrescine, which can be further converted to two polyamines: spermidine and spermine. The inventor thus has also tested the protective effect of L-ornithine and spermidine on endotoxic shock. The results show that L-ornithine and spermidine also protect against endotoxic shock, as disclosed in the above-mentioned patent applications.

Among the above described series materials, putrescine and spermine have not been tested for the protective effect against endotoxic shock. The inventor has further found that spermine shows no protective effect, while putrescine exhibits a protective effect against endotoxic shock.

SUMMARY OF THE INVENTION

Therefore, the object of the present invention is to provide a method for protecting a living subject from endotoxic shock. The method includes administering to the subject an effective amount of putrescine and a pharmaceutically acceptable carrier.

DETAILED DESCRIPTION OF THE INVENTION

According to the present invention, upon administering an effective amount of putrescine, the survival rates of mice infected with endotoxic shock can be greatly increased. The results indicate that putrescine is effective for protecting mice from endotoxic shock.

Putrescine, the active ingredient, can be admixed with a pharmaceutically acceptable carrier, so that it can be administered parenterally in sterile liquid dosage forms, such as injected intraperitoneally, it can also be administered orally in liquid dosage forms, such as elixirs, syrups, and suspensions, or in solid dosage forms, such as capsules, tablets, and powders.

The following examples serve to demonstrate the pharmacological activities of the claimed pharmaceutical composition. These are not intended as limiting since numerous modifications and variations will be apparent to those skilled in the art.

EXAMPLE

The mice used in this example were Balb/c having a body weight of 24 ±1.0 g. E. coli LPS (serotype 0111:B4, purchased from Sigma) dissolved in phosphate buffered saline (PBS) (0.01M sodium phosphate, 0.15M NaCl, pH 7.4) was used for inducing endotoxic shock. Putrescine purchased form Sigma was also dissolved in PBS.

Putrescine (10 mg/mouse) was intraperitoneally injected 48 hours and 24 hours before, at the same time of, and 24 hours after LPS injection (0.9 mg/mouse) to observe the survival rate of the mice injected with putrescine at different times. The survival rates were analyzed by the Fisher's exact test. As shown in Table 1, the maximum survival rate was observed when putrescine was injected 24 hours prior to LPS injection, attaining 40% ($P< 0.1$).

TABLE 1

|  | time course of putrescine injection (hours)* | | | |
|---|---|---|---|---|
|  | −48 | −24 | 0 | 24 |
| survived/total | 1/15 | 6/15 | 2/15 | 0/15 |
| survival rate (%) | 6.7 | 40 | 13 | 0 |
| P value+ |  | 0.08 | 1.0 | >1.0 |

*LPS was injected at time zero.
+compared with the control case in which putrescine was injected 48 hours prior to LPS injection Various doses of putrescine were injected 24 hours prior to LPS injection (0.9 mg/mouse). The survival rates are shown in Table 2, indicating that the maximum survival crate was observed when a dosage of 10 mg of putrescine per mouse was injected, attaining 53% ($P< 0.01$).

TABLE 2

|  | putrescine dose (mg/mouse) | | | | |
|---|---|---|---|---|---|
|  | 0 | 1 | 3 | 10 | 30 |
| survived/total | 5/30 | 10/30 | 11/30 | 16/30 | 11/30 |
| survival rate (%) | 17 | 33 | 37 | 53 | 37 |
| P value+ |  | 0.23 | 0.14 | 0.006 | 0.14 |

+compared with the control case where no putrescine was added

What is claimed is:

1. A method for protecting a living subject from endotoxic shock, comprising administering to said subject a pharmaceutical composition which comprises an effective amount of putrescine and a pharmaceutically acceptable carrier.

2. The method as claimed in claim 1, wherein the pharmaceutically acceptable carrier is phosphate buffered saline.

3. The method as claimed in claim 1, wherein the pharmaceutical is composition administered by intraperitoneal injection.

4. The method as claimed in claim 1, wherein the pharmaceutical composition is administered parenterally.

5. The method as claimed in claim 1, wherein the pharmaceutical composition is administered orally in a liquid dosage form.

6. The method as claimed in claim 1, wherein the pharmaceutical composition is administered orally in a solid dosage form.

* * * * *